(12) United States Patent
Pollitt et al.

(10) Patent No.: US 6,303,340 B1
(45) Date of Patent: Oct. 16, 2001

(54) METHOD FOR PRODUCING A PEPTIDE WITH A PI ABOVE 8 OR BELOW 5

(75) Inventors: N. Stephen Pollitt, Los Altos; Douglas I. Buckley, Woodside; Peter A. Stathis; Taymar E. Hartman, both of Menlo Park; Ziyang Zhong, Union City, all of CA (US)

(73) Assignee: Scios Inc., Sunnyvale, CA (US)

( * ) Notice: Subject to any disclaimer, the term of this patent is extended or adjusted under 35 U.S.C. 154(b) by 0 days.

(21) Appl. No.: 09/349,644

(22) Filed: Jul. 8, 1999

Related U.S. Application Data
(60) Provisional application No. 60/092,423, filed on Jul. 10, 1998.

(51) Int. Cl.$^7$ .................................................. C12P 21/04
(52) U.S. Cl. .................... 435/69.7; 435/69.7; 435/69.1; 435/69.3; 435/69.2; 435/6; 435/7.1; 435/320.1; 435/172.3; 435/189; 435/195; 530/350; 536/23.1; 536/23.4; 536/24.5; 514/2; 514/12
(58) Field of Search ................ 435/69.1, 320.1, 435/69.7, 172.3, 189, 69.3, 6, 195, 69.2, 7.1; 536/23.4, 24.5, 23.1; 530/350; 514/12, 2

(56) References Cited

U.S. PATENT DOCUMENTS

| | | | |
|---|---|---|---|
| 5,093,241 | * 3/1992 | Bennett et al. | 435/69.4 |
| 5,114,923 | 5/1992 | Seilhamer et al. | 514/12 |
| 5,589,364 | 12/1996 | Williams et al. | 435/65.7 |
| 5,595,887 | * 1/1997 | Coolidge et al. | 435/69.7 |

FOREIGN PATENT DOCUMENTS

| | | | | |
|---|---|---|---|---|
| 0131363A1 | * | 1/1985 | (EP) | 530/350 |
| 0528686A2 | * | 2/1993 | (EP) | 530/350 |
| WO92/02550 | * | 2/1992 | (WO) | 530/350 |
| 92/15682 | | 9/1992 | (WO). | |
| 97/35009 | | 9/1997 | (WO). | |

OTHER PUBLICATIONS

Monsalve et al. Structural analysis of the small chain of the 2S albumin, napin nlll, from rapeseed, 1991.*

Marcus, F. (1984) Preferential cleavage at aspartyl–prolyl peptide bonds in dilute acid. Int. J. Peptide Protein Res. 25, 1985, 542–546.

Wanner, B.L. (1994) Phosphorus assimilation and control of the phosphate regulon. *Escherichia coli* and *Salmonella* Cellular and Molecular Biology Second Edition, vol. 1, 1357–1381.

Wilkinson, D.L. et al. (1991) Predicting the solubility of recombinant proteins in *Escherichia coli*. Bio/Technology vol. 9: 443–447.

* cited by examiner

*Primary Examiner*—Karen Cochrane Carlson
*Assistant Examiner*—Hope A. Robinson
(74) *Attorney, Agent, or Firm*—Knobbe, Martens, Olson & Bear LLP (57) ABSTRACT

A method is described for producing a peptide having a pI above 8 or below 5 wherein the peptide is expressed as a fusion protein in which it is linked to a fusion partner through an acid cleavage site. The peptide is released from the fusion partner by acid cleavage in the absence of chaotrope. The fusion partner and its acid cleavage products, if any, have a net charge sufficiently different from that of the desired peptide to allow isolation of the peptide by ion-exchange chromatography.

27 Claims, 6 Drawing Sheets

```
                                10                                      20
 1 MetGluLysLysIleThrGlyTyrThrThrValAspIleSerGlnTrpHisArgLysGlu
 1 MetGluLysLysIleThrGlyTyrThrThrValAspIleSerGlnTyrHisValLeuGlu 30                                      40
21 HisPheGluAlaPheGlnSerValAlaGlnCysThrTyrAsnGlnThrValGlnLeuAsp
21 HisPheGluAlaPheGlnSerValAlaGlnSerThrTyrAsnGlnThrValGlnLeuAsp 50                                      60
41 IleThrAlaPheLeuLysThrValLysLysAsnLysHisLysPheTyrProAlaPheIle
41 IleThrAlaPheLeuGluThrValGluValAsnValHisLeuPheTyrProAlaPheIle 70
61 HisIleLeuAlaArgLeuMetAsnAlaHisProGluPheArgMetAlaMetLys
61 HisIleLeuAlaValLeuLeuAsnAlaHisProLeuPheThrGlyGlyProAsp
```

FIG. 1

```
Wild Type phoA   TGTTTTTATTTTTTAATGTATTTGTACATGGAGAAAATAAA    GTG pTH85            TGTTTTTATTTTTTAATGTATTTGTACAA GAGG    CTTCCATATG
```

METHOD FOR PRODUCING A PEPTIDE WITH A PI ABOVE 8 OR BELOW 5

CROSS-REFERENCE TO RELATED APPLICATIONS

This is a non-provisional application of co-pending provisional application Serial No. 60/092,423 filed on Jul. 10, 1998, the disclosure of which is hereby incorporated by reference and to which application priority is claimed under 35 USC 119.

FIELD OF THE INVENTION

This invention relates to methods and reagents useful in the production of peptides. In particular, the invention relates to the production of peptides which have pI's below about 5 or above about 8. A preferred embodiment of the invention relates to the production of b-type natriuretic peptide.

BACKGROUND OF THE INVENTION

The present invention is directed to efficient methods for expressing and recovering a peptide, particularly when the peptide one desires to produce has a high pI or a low pI, which makes it desirable to employ ion exchange chromatography as a step in the purification of the peptide. The invention will be exemplified with respect to b-type natriuretic peptide, which has a relatively high pI. Nonetheless, those skilled in the art will appreciate that the methods and reagents disclosed herein will have applicability to the production of other peptides having either a high or low pI.

It is well known in the art that the production of peptides of less than about 50 amino acids in length by expression of peptide-encoding DNA in a recombinant host cell such as *E. coli* is commonly plagued by the problem of enzymatic degradation of the expressed peptide within the host cell, resulting in partial or complete loss of the peptide. The most commonly employed means to overcome this problem is to insolubilize the peptide within the host cell. This can be effected by expressing the peptide as a fusion protein in which the peptide is linked to a fusion partner. Normally, the fusion partner will be fused to the N-terminus of the peptide. The fusion protein forms inclusion bodies within the cell, within which the peptide is protected from degradation by proteolytic enzymes.

Once the inclusion bodies are recovered from the host cell, the peptide must be separated from the leader sequence, purified and recovered in an active form. Separation from the leader sequence may be accomplished by placing a sequence of amino acids at the junction of the leader and the peptide which are specifically recognized and cleaved under appropriate conditions, e.g. acid cleavage or enzymatic cleavage. Enzymatic cleavage is frequently impractical for commercial scale production due to the enzyme's high cost and limited useful lifetime, even when employed on an immobilized column.

Acid cleavage can be accomplished by placing a specific dipeptide at the junction of the leader sequence and the peptide, wherein the first amino acid in the dipeptide is aspartic acid. Selection of the second amino acid will determine the rate at which the dipeptide bond is cleaved under acidic conditions. Of course, if the desired peptide contains any internal dipeptide sequences that are acid cleavable, then the cleavage site at the junction of the leader and the peptide must undergo acid cleavage at a substantially greater rate than the internal cleavage in order to avoid unacceptable loss of yield. The relative reaction rates of acid cleavable dipeptides are as follows:

| Dipeptide | Rel. rxn. rate |
| --- | --- |
| Asp-Pro* | 10x |
| Asp-X | 1x |
| X = Gly*, Ser*, Leu,*Ile, Val | |
| Asp-Lys* | 0.5x |
| Asp-Arg** | 0.2x |

*F. Marcus, Intl. J. Peptide and Protein Res. (1985) 25: 542–546
**Our observations Prior to enzymatic or acid cleavage, the fusion protein in the inclusion bodies is normally solubilized by treatment with a chaotropic agent which causes unfolding of the protein structure. The solubilized fusion protein is then cleaved, the desired peptide is isolated and purified, and the peptide is subjected to conditions which cause it to refold into a biologically active conformation, such as by removal of the chaotrope and oxidation, if necessary to cause formation of internal disulfide bonds.

The peptide known as b-type natriuretic peptide or BNP occurs in humans as a 32-amino acid peptide which is produced in vivo by the cleavage of a 134-amino acid precursor protein. The DNA sequence encoding the human b-type natriuretic precursor has been isolated (U.S. Pat. No. 5,114,923). B-type natriuretic peptide has been shown in human clinical trials to improve heart function without direct cardiac stimulation (which may cause harmful side effects such as arrhythmias) and to decrease levels of neurohormones associated with increased mortality and acceleration of the progression of heart failure. Accordingly, it is useful in the treatment of congestive heart failure patients.

While b-type natriuretic peptide offers certain clinical advantages over other drugs used to treat congestive heart failure patients, the relatively high cost of production of peptide drugs compared with non-peptide drugs could present an impediment to its acceptance in clinical practice. Consequently, there is a need to provide a highly efficient means of producing b-type natriuretic peptide in order to minimize its cost. Recombinant production of the peptide in the form of inclusion bodies presents several problems. The use of enzymatic cleavage of a fusion protein to yield b-type natriuretic peptide is undesirable because of the high cost of the enzymes that would be required. If one wishes to take advantage of the relatively high pI of b-type natriuretic peptide ($\geq 10$) by using ion exchange chromatography as a purification step, then the use of an ionic chaotrope such as guanidine hydrochloride is to be avoided, since the ionic chaotrope will interfere with the ion exchange chromatography. On the other hand, urea, the most commonly used non-ionic chaotrope, is problematical if one is to employ acid cleavage of the fusion protein. Under high temperature acidic conditions, the presence of urea causes the degradation of the peptide.

SUMMARY OF THE INVENTION

In the present invention, acid cleavage of the fusion protein is conducted in the absence of chaotropes, resulting in soluble b-type natriuretic peptide. The soluble peptide can be separated from the fusion partner and other contaminants, which remain insoluble, using any convenient method known for separating soluble proteins from insoluble proteins, e.g. by ultrafiltration, diafiltration or centrifugation. Since ultrafiltration and centrifugation are suboptimal steps from a commercial point of view, a preferred embodiment of the invention employs solubilization of the insoluble materials, following cleavage, by treatment with a non-ionic chaotrope such as urea, and isolation of b-type natriuretic peptide by ion-exchange chromatography.

The present invention provides an efficient method for producing a peptide having a pI above about 8 or below about 5. A preferred embodiment of the method of the invention comprises the steps of:

(a) expressing said peptide, in a recombinant host cell as a fusion protein in which the desired peptide is fused at its N-terminus to a fusion partner comprising an amino acid sequence having an Asp residue at its C-terminus, wherein (i) the C-terminal Asp residue of the fusion partner and the N-terminal residue of the peptide form a bond which is cleavable under acidic conditions, (ii) the peptide has a sufficiently different net charge from that of the fusion partner and any undesired fragments produced by acid cleavage of the fusion protein that the peptide is capable of being separated from the fusion partner and any undesired acid cleavage fragments of the fusion protein by ion-exchange chromatography and (iii) the fusion protein forms inclusion bodies within the recombinant host cell;

(b) recovering the inclusion bodies from the recombinant host cell;

(c) cleaving the peptide from the fusion partner by subjecting the fusion protein to acidic conditions in the absence of a chaotrope;

(d) solubilizing the insoluble cleavage products by treating them with a non-ionic chaotrope under conditions which cause them to become solubilized without degrading the primary structure of the peptide; and (e) isolating the peptide by ion-exchange chromatography.

There is also provided herein an expression vector which is useful for expressing a fusion protein that is cleavable under acid conditions to yield a desired peptide having a pI above 8 or below 5, said vector comprising:

(a) a regulatory sequence capable of directing expression of the fusion protein in the host cell;

(b) a DNA sequence encoding at least a portion of the amino acid sequence of modified chloramphenicol acetyl transferase in which a sufficient number of codons encoding lysine, arginine and/or histidine residues have been replaced with codons encoding uncharged or negatively charged amino acids that the pI of the fusion protein is between 6.0 and 8.0;

(c) a codon encoding aspartic acid, which is linked to the 3' end of the DNA sequence encoding modified chloramphenicol acetyl transferase, either directly or through a linker sequence; and (d) a DNA sequence encoding the desired peptide having a pI above 8 or below 5 and having a proline, glycine, serine, leucine, alanine, isoleucine or valine residue at its N-terminus, said sequence being linked at its 5' end to the 3' end of the DNA sequence encoding the modified chloramphenicol acetyl transferase.

DETAILED DESCRIPTION OF THE INVENTION

A. The Production Method of the Invention

The method of the invention is used to produce purified peptides having pI's above about 8 or below about 5. While the invention is exemplified herein with respect to b-type natriuretic peptide, which has a relatively high pI, it will be appreciated that the method of the invention is also applicable to the production of peptides with low pI's, provided that the desired peptide has a sufficiently different net charge from that of the fusion partner and any undesired fragments produced by acid cleavage of the fusion protein (i.e., fragments produced by cleavage at sites other than the junction of the fusion partner and the desired peptide) to allow the desired peptide to be isolated from the cleavage mixture by ion exchange chromatography. The difference in net charge between the peptide and the other cleavage products, including any intact fusion partner in the cleavage mixture, is preferably at least about ±2, more preferably at least about ±3. Thus, if a fusion partner is selected which has one or more internal acid cleavage sites, then each of the cleavage products of the fusion partner should have a net charge that is sufficiently different from that of the desired peptide that it can be separated from the peptide by ion exchange chromatography.

The fusion partner is also selected with consideration given to the formation of inclusion bodies by the fusion protein. The selection of an appropriate fusion partner for this purpose will depend, in part, upon the nature of the peptide being produced. Preferably, the fusion partner contains at least about 50 amino acid residues. While there is no strict upper limit on the number of amino acid residues in the fusion partner, it is preferred not to exceed about 100, since a larger number of amino acid residues in the fusion partner generally translates into a lower yield of the desired peptide. It is also preferred to select a fusion partner such that the fusion protein contains about 25 to about 50 hydrophobic amino acid residues, which promote the formation of inclusion bodies.

The fusion partner has an Asp residue at its C-terminal end where it joins the N-terminal end of the peptide.

Preferably, the fusion partner is selected such that the pI of the fusion protein is between 6.0 and 8.0, more preferably between 6.5 and 7.5. A particularly preferred fusion partner of the invention contains at least an N-terminal portion of a modified chloramphenicol acetyl transferase. The amino acid sequence of the chloramphenicol acetyl transferase is modified to replace a sufficient number of lysine, arginine and/or histidine residues with uncharged or negatively charged amino acids that the fusion protein has a pI between 6.0 and 8.0, preferably between 6.5 and 7.5. Additional modifications that may be made to the chloramphenicol acetyl transferase sequence include: (a) replacement of the cysteine, tryptophan and methionine residues by residues other than cysteine, tryptophan and methionine; and (b)

replacement of one or more acidic or basic residues with hydrophobic residues as required to achieve charge balance.

Replacement of the tryptophan, cysteine and methionine residues serves to eliminate undesirable oxidative side reactions which could involve the desired peptide. Substitution of hydrophobic residues for lysine, arginine and/or histidine both reduces the pI and percentage of charged residues of the fusion partner and introduces hydrophobicity which promotes inclusion body formation. The Asp residue at the C-terminal end of the modified chloramphenicol acetyl transferase sequence may be linked to the chloramphenicol acetyl transferase sequence directly or through a linker sequence. A linker sequence may be present as a result of translation of codons inserted into the expression vector to provide a restriction site. If the peptide which one wishes to produce by the method of the invention contains an internal acid cleavage site, then the acid cleavage site formed at the junction of the fusion partner and the peptide must be one which has a higher rate of reaction than the internal cleavage site, as indicated supra. For example, human b-type natriuretic peptide contains an internal Asp-Arg dipeptide which is susceptible to acid cleavage. In accordance with the present invention, we have expressed this peptide as a fusion with a modified chloramphenicol acetyl transferase sequence, wherein the junction of the fusion partner and the b-type natriuretic peptide forms an Asp-Ser dipeptide. Due to the differential rates of acid cleavage of the two dipeptides, we have been able to obtain good yields of the desired peptide, notwithstanding the loss of some peptide by cleavage at the internal cleavage site. Alternatively, we have utilized the procedure of the invention to produce b-type natriuretic peptide (2-32). This molecule has biological activity equivalent to that of the full-length 32-amino acid form and, due to the presence of proline at its N-terminus, results in even more efficient cleavage from the fusion partner, with concomitant enhancement of yield.

The fusion protein is expressed in a host cell using known techniques of recombinant DNA production. Any suitable host cell known to be useful for the expression of proteins by recombinant DNA methods may be employed, including prokaryotic and eukaryotic host cells and cell lines. *E. coli* is a preferred host cell. The host cell contains an expression vector which encodes the fusion protein under the control of a regulatory sequence which is capable of directing its expression in the host, as well as an origin of replication that is functional in the host cell. The vector may contain other DNA sequences conventionally employed in recombinant DNA technology such as sequences encoding selectable markers.

The host cell containing the expression vector is grown and the fusion protein expressed under appropriate conditions. The conditions for growth of the host cell and expression of the fusion protein will vary depending on various factors such as the host cell employed, the promoter and the particular fusion protein being expressed. Those skilled in the art are capable of determining the appropriate conditions for the particular host/vector system employed.

After the fusion protein has been expressed in the form of inclusion bodies, the inclusion bodies are recovered from the host cells. This can be accomplished by known methods such as, for example, by lysing the cells chemically or mechanically and separating the inclusion bodies by centrifugation. Typically, we dilute a cell paste in several volumes of a lysis buffer and lyse the cells by multiple passage through an AVP Gaulin homogenizer at 9,000–10,000 psi. The cell lysate is then further diluted in buffer and centrifuged to recover the inclusion bodies.

The inclusion bodies are then subjected to acid conditions to cleave the fusion partner from the desired peptide. Acid cleavage is performed in the absence of a chaotrope in order to avoid subjecting the peptide to conditions which would cause its degradation. Cleavage can be effected by suspending the inclusion bodies in an aqueous acid solution at elevated temperature. Preferably, the inclusion bodies are suspended at between 5% and 15% w/v, more preferably between 5% and 8% w/v, in an acid solution at a pH between about 1.7 and 2.2, preferably between 1.9 and 2.1. HCl is a preferred acid for carrying out the cleavage, however, other acids may be employed, including by way of example acetic acid and phosphoric acid. Cleavage is carried out at a sufficient temperature and for a sufficient time to maximize yield. Typically, the cleavage is carried out at a temperature from about 75° C. to about 95° C. for a period from about 2 hrs to about 10 hrs. In the production of b-type natriuretic peptide, we conducted acid cleavage by diluting the inclusion bodies to 10% w/v in water, adjusting the pH to 2.0 with HCl and maintaining at 85° C. for 4.5–5.5 hours, preferably.

Because ultrafiltration and precipitation are suboptimal steps from a commercial production standpoint, it is preferred that, following cleavage, the fusion partner and peptide are solubilized by treating them with a non-ionic chaotrope, preferably urea, and the peptide is then isolated by ion-exchange chromatography. The suspension is preferably cooled to 50° C. or below, for instance, below 40° C. before adding the chaotrope. Solubilization can be carried out by adding solid urea to a concentration of about 3 M to about 7 M and maintaining at a temperature below 40° C., preferably at about room temperature (18–25° C.).

After adjustment of the pH to 3 and 7.5, preferably 3.8–4.2, the solution containing the cleaved fusion partner and peptide can then be loaded directly onto an ion-exchange column. Any commercially available ion-exchange column suitable for the peptide being isolated may be employed. For b-type natriuretic peptide, we employed a sulfopropyl ion-exchange column (Pharmacia Streamline®). The column is equilibrated and washed to elute contaminants. The desired peptide is then eluted from the column using an appropriate salt concentration. For b-type natriuretic peptide, elution from the column was effected with a 0.5–0.6 M, preferably NaCl solution.

In many cases, the peptide recovered from the ion exchange column will refold into its native conformation, however, additional steps may be required to restore the peptide to a biologically active form, particularly when the peptide requires the formation of internal disulfide bonds for activity. B-type natriuretic peptide contains two cysteine residues that must be disulfide bonded. This can be accomplished by subjecting the recovered peptide to oxidation conditions. Oxidation can usually be effected by subjecting a solution of the peptide to heat and stirring under air. Alternatively, oxidants such as $Cu^{+2}$, $I_3^-$ or $Fe(CN)_6^{-3}$ can be employed.

If desired, further purification steps can be employed using techniques known to those skilled in the art. Such steps may include, for example, HPLC, such as RP-HPLC or additional ion exchange chromatography steps. In the case of b-type natriuretic peptide, the recovered peptide was subjected to RP-HPLC, in ammonium acetate buffer pH 5.0–5.5 and an acetonitrile elution gradient.

B. The Expression Vector of the Invention

The present invention also provides an expression vector suitable for carrying out the production method of the invention. The expression vector utilizes a DNA sequence encoding at least an N-terminal portion of the amino acid sequence of chloramphenicol acetyl transferase (CAT) which has been modified such that a sufficient number of codons for lysine, arginine and/or histidine residues have been replaced by codons for uncharged or negatively charged amino acids such that the pI of the fusion protein is between 6.0 and 8.0, preferably between 6.5 and 7.5 Advantageously, some of the lysine, arginine and/or histidine residues can be replaced with hydrophobic residues, which not only reduce the net charge of the fusion partner, but also promote the formation of inclusion bodies within the host cell. If desired, one or more codons for tryptophan, cysteine and/or methionine residues in the native sequence of CAT can be replaced by codons for residues other than tryptophan, cysteine or methionine in order to prevent undesirable oxidative side reactions, e.g. disulfide bonding with b-type natriuretic peptide, provided the resulting fusion protein has a pI in the required range.

Figure 1:
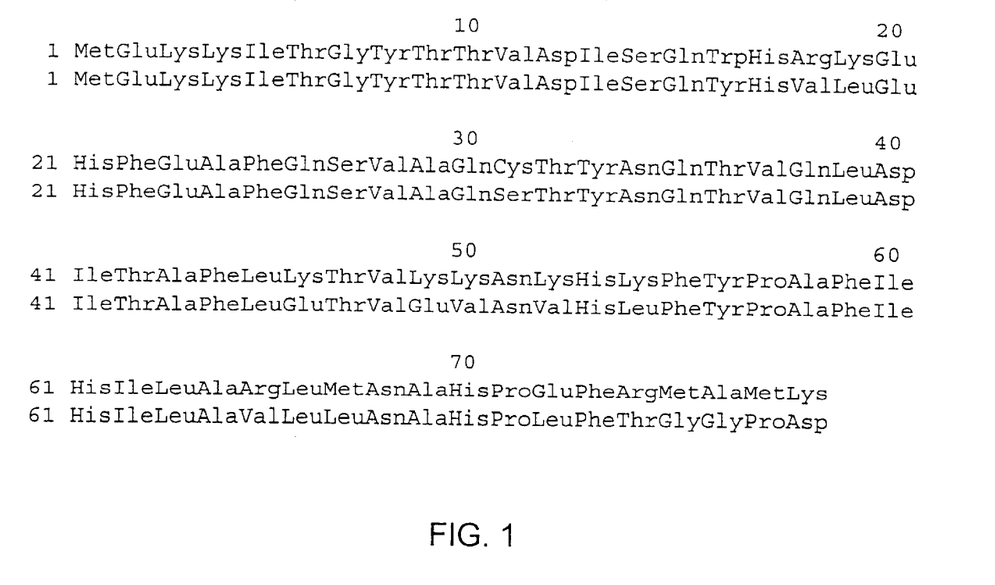
FIG. 1 shows the amino acid sequence of a modified chloramphenicol acetyl transferase (SEQ ID NO:11) on the lower line and the wild-type chloramphenical acetyl transferase (SEQ ID NO:12) on the upper line used as a fusion partner to produce b-type natriuretic peptide.

In FIG. 1, the amino acid sequence on the top line represents the native amino acid sequence of the first 78 amino acids from the N-terminus of CAT. The bottom line represents the modified CAT sequence which was encoded by the vector which we used to express a fusion protein suitable for the production of b-type natriuretic peptide. The five amino acids of the modified sequence beginning with Thr (position 74) represent a linking sequence joining the C-terminal Asp to the modified CAT sequence and introducing an AgeI site. The AgeI site was produced by mutating the codons for amino acids 74 and 75.

Figure 2:
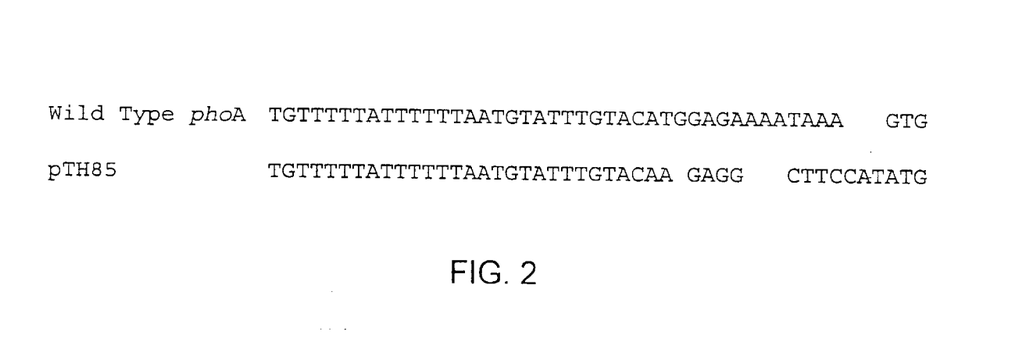
FIG. 2 shows the DNA sequence of the wild-type phoA promoter on the SEQ ID NO: 13) upper line and the modified phoA promoter (SEQ ID NO:14) on the bottom line.

In the vector of the invention, the modified CAT encoding DNA sequence is under the control of a regulatory sequence which is capable of directing expression of the fusion protein in the host cell. Any suitable promoter may be employed, for example a trpLE, phoA or lacZ promoter. A preferred promoter is the *E. coli* phoA promoter described by Wanner, B. L. in *Escherichia coli and Salmonella*, $2^{nd}$ edition (Neidhardt, P. C. et al. Eds., ASM Press, Washington, D.C.) pp. 1357–1381. This promoter initiates transcription of the fusion protein encoding DNA sequence in the absence of phosphate in the growth medium. The phoA promoter which we employed was mutated from the native *E. coli* phoA sequence (SEQ ID NO:13) to substitute an ATG translation initiation signal for the native GTG signal. FIG. 2 shows the DNA sequence of the wild-type phoA promoter on the upper line and the modified phoA promoter (SEQ ID NO:14) employed by us to produce the expression vector for b-type natriuretic peptide on the bottom line.

The DNA sequence encoding the desired peptide is linked at its 5' end to the Asp codon at the 3' end of the fusion partner. The DNA sequence encoding the peptide has, at its 5' end, a codon for Pro, Gly, Ser or Leu. The particular amino acid chosen will depend in part on the sequence of the desired peptide. If the peptide contains one or more internal acid cleavage sites, then the N-terminal amino acid must be selected such that the cleavage site at the junction of the fusion partner and the peptide is cleaved at a rate greater than that of the internal cleavage site. If the native sequence of the desired peptide does not contain a Pro, Gly, Ser or Leu codon at its N-terminus, then the DNA encoding the peptide is modified by placing a codon for the desired amino acid at the 5' end. It will be appreciated that this will result in an extraneous amino acid at the N-terminus of the peptide following cleavage from the fusion partner, which may be acceptable if it does not interfere with biological activity. In the case of b-type natriuretic peptide, the N-terminal amino acid is Ser. This amino acid is acceptable at the junction with the fusion partner, since b-type natriuretic peptide contains only one internal acid cleavage site, Asp-Arg, which is cleaved at a much lower rate than Asp-Ser.

The expression vector of the invention can be prepared and incorporated into a host cell using well known techniques of DNA recombination.

The following non-limiting examples are intended to further illustrate the practice of the invention described herein. The plasmid pCB101-1 (Example 1) in an *E. coli* W3110 host has been deposited at the American Type Culture Collection, Manassas, Va., with accession no. ATCC 98774. The plasmid pTH76 (Example 1), in an *E. coli* W3110 host has been deposited at the American Type Culture Collection, Manassas, Va., with accession no. ATCC 98775 The plasmid pTH53 (Example 2) in an *E. coli* W3110 host has been deposited at the American Type Culture Collection, Manassas, Va., with accession no. ATCC 98776.

EXAMPLE 1

Synthesis and Cloning of a Gene Encoding a Fusion Protein to B-type Natriuretic Peptide The tetracycline resistance plasmid pCB 101–1 (5 μg), encoding the trp promoter and a fusion protein consisting of the b-type natriuretic peptide fused to the 3' end of a modified 153 amino acid N-terminal portion of chloramphenicol acetyl transferase, was digested with NdeI and AgeI. The resulting digest was subjected to electrophoresis on a 1% agarose gel (SeaPlaque, FMC, Rockland, Me.) and the 3.4 Kbp fragment was excised.

Oligonucleotides were synthesized having the following sequences:
Oligo 1099:
TATGGAGAAAAAAATCACTGGATATAC-
CACCGTTGAT (SEQ ID NO:1)
Oligo 1100:
CAGAACATGATATTGGGATATATCAACG-
GTGGTATATCCAGTGATTTTTTTCTCCA (SEQ ID NO:2)
Oligo 1101:
ATATCCCAATATCATGTTCTGGAA-
CATTTTGAGGCATTTCAGTCAGTTGCT-
CAATCAACC (SEQ ID NO:3)
Oligo 1102:
TATAACCAGACCGTTCAGCTGGATAT-
TACGGCCTTTTTAGAAACCGTAGAAGTTAATGTT (SEQ ID NO:4)
Oligo 1103:
AAAGGCCGGATAAAACAGGTGAACAT-
TAACTTCTACGGTTTCTAAAAAGGCCGTAATATC (SEQ ID NO:5)
Oligo 1104:
CAGCTGAACGGTCTGGTTATAGGT-
TATTAGAGCAACTGACTGAAATGCCT-
CAAAATGTTC (SEQ ID NO:6)
Oligo 1105:
CACCTGTTTTATCCGGCCTTTATTCA-
CATTCTTGCCGTTCTGCTGAATGCT-
CATCCGCTGTTCA (SEQ ID NO:7)
Oligo 1106:
CCGGTGAACAGCGGATGAGCATTCAGCA-
GAACGGCAAGAATGTGAAT (SEQ ID NO:8)
Oligonucleotides 1100–1105 (1μg each) were individually phosphorylated by treatment with ATP and $T_4$ polynucleotide kinase and combined with 1 μg each of oligonucleotides 1099 and 1106. The oligonucleotide mixture was then denatured by boiling for 7 minutes and allowed to gradually cool to room temperature. Five µl of this 214 µl reaction mixture was ligated to 1.5 µl of the melted excised fragment of pCB101-1 prepared above using $T_4$ DNA ligase at room temperature overnight. The mixture was then re-melted and used to transform the *E. coli* strain MC1061 to tetracycline resistance. Eight of the resulting colonies were screened for plasmids having a 317 bp AgeI/MluI fragment. One such plasmid was designated pTH80, encoding a modified CAT sequence fused to b-type natriuretic under the control of trp.

Figure 3:
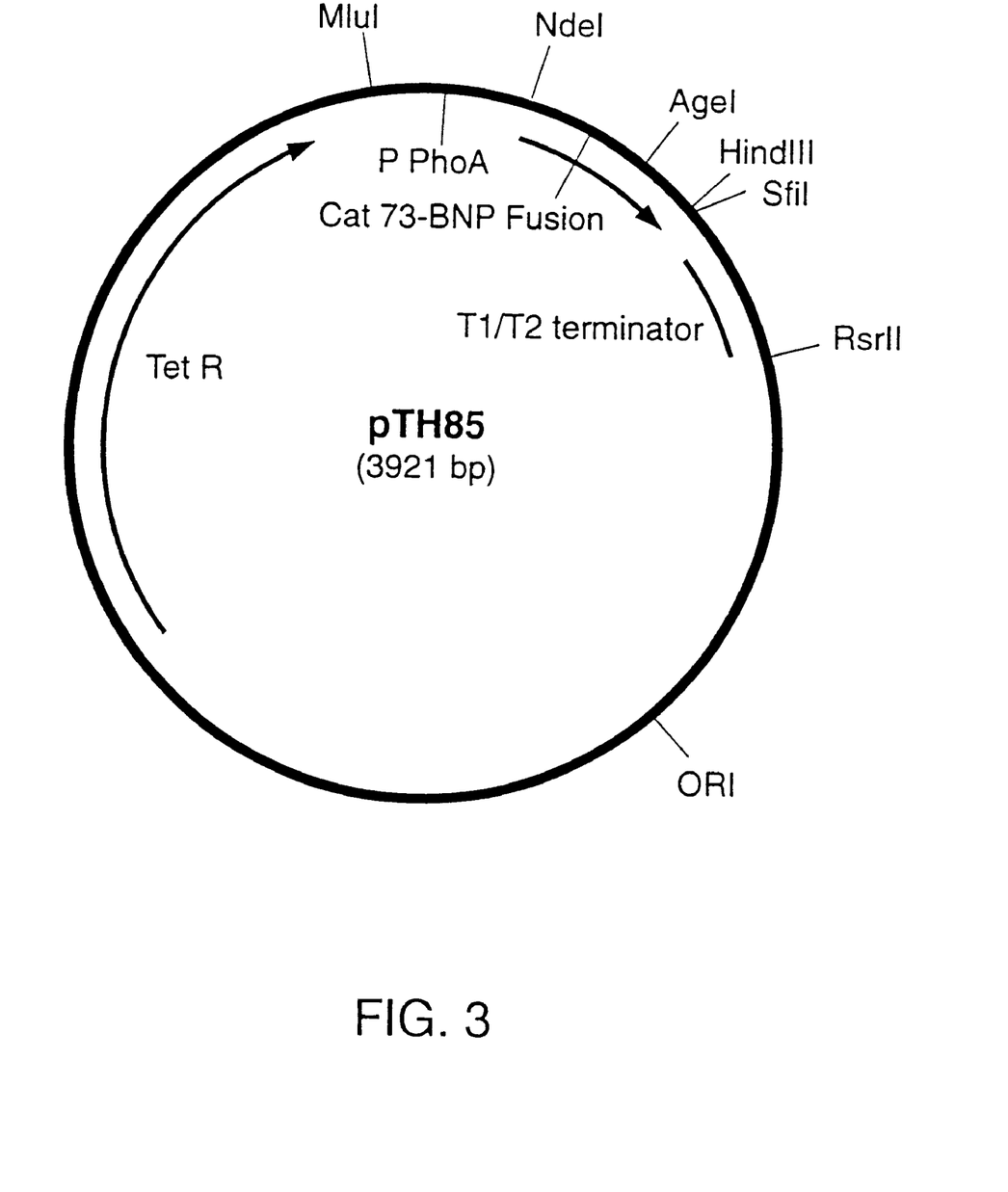
FIG. 3 is a plasmid diagram of pTH85.

It is important to be able to control synthesis of the fusion protein during fermentation. The phoA promoter has the advantage of being able to maintain the target gene in an uninduced state until full induction is achieved by depletion of $PO_4$. To place the fusion under the control of the phoA promoter, pTH80 was digested with restriction enzymes NdeI and HindIII. The digest was then electrophoresed on a 3% agarose gel (NuSieve, FMC, Rockland, Me.), and the 332 bp fragment encoding the CAT-BNP fusion was excised. The vector fragment was prepared by digestion of the tetracycline resistance plasmid, pTH76, with NdeI and HindIII. pTH76 is very similar to pTH80 except that the trp promoter is replaced by the phoA promoter. The vector fragment was isolated by digestion of 2.4 µg of pTH76 with NdeI and HindIII at 37° C. overnight followed by treatment with calf intestinal phosphatase at 37° C. for one hour. Final volume of the reaction mixture was 100 µl. A ligation was performed between 1 µl of the vector fragment and 3 µl of melted excised gel slice containing the insert fragment from pTH80. After overnight incubation at room temperature, the mixture was used to transform strain W3110. DNA prepared from the resulting colonies was screened for the presence of a unique BstXI site. Three positive clones were confirmed by DNA sequencing. One of these was designated pTH85. FIG. 3 is a plasmid diagram of pTH85.

Plasmid pTH85 and two other positive clones from its construction were used to transform *E. coli* strain W3110 to tetracycline resistance. Single colonies were inoculated into L broth with 6.25 µg/ml tetracycline. After 4 hours incubation at 37° C., the resulting culture was used to inoculate a culture containing the following media to an optical density of 0.1:

| | |
|---|---|
| Glucose | 4 g |
| Casamino Acids | 5 g |
| 1M Potassium MOPS buffer, pH 7.4 | 40 ml |
| $(NH_4)_2SO_4$ | 1.24 g |
| 1M $MgSO_4$ | 2 ml |

After overnight incubation at 37° C., all cells could be observed under phase contrast microscopy to have at least one phase bright inclusion body. Cells were recovered and boiled for 18 minutes in SDS sample buffer and electrophoresed on a standard Laemmli Tris-glycine SDS polyacrylamide gel. Abundant accumulation of the b-natriuretic peptide fusion protein is indicated by the presence of a heavy Coomassie staining band migrating at approximately 12 Kdaltons.

EXAMPLE 2

Cloning of a Gene Encoding a Fusion Protein to b-type Natriuretic Peptide (2-32)

Acid cleavage occurs most rapidly at an Asp-Pro peptide bond. Since the second residue of mature b-type natriuretic peptide is Pro, it is possible to facilitate cleavage of b-type natriuretic peptide from the fusion partner by expressing a truncated version of b-type natriuretic peptide comprising amino acid residues 2-32 [b-type natriuretic peptide (2-32)]. A altered form of the AgeI/HindIII restriction fragment lacking the initial serine codon of mature b-type natriuretic peptide was constructed by PCR of the wild type coding sequence using the following two oligonucleotides as PCR primers:

Oligo 754:
GTGGTGGTACCGGTGGTGACCCGAAAATGGTTCAG (SEQ ID NO.:9)

Oligo PR1279:
CCTACTCTCGCATGGGGAGA (SEQ ID NO:10)

A 100 µl reaction mixture was prepared containing 0.4 mM of each dNTP, 1.3 µg of each primer, 50 ng of plasmid pTH53 carrying the b-type natriuretic peptide sequence fused to the 3' end to a clone of human ubiquitin, and 1 µl of VENT DNA polymerase (New England Biolabs, Beverly, Mass.) in a reaction buffer provided by the manufacturer. The reaction was carried out for 30 cycles of the following temperature program: 94° C. for 1 minute, 55° C. for 2 minutes, and 72° C. for 1 minute. The anticipated size, 167 bp, was verified by agarose gel electrophoresis on 3% Nusieve. The PCR reaction product, along with vector plasmid pTH53, was then subjected to double digestion with KpnI and HindIII. The vector digest was then further treated with calf intestinal phosphatase for 45 minutes at 37° C. followed by phenol extraction and ethanol precipitation. The plasmid digest was then resuspended in 30 µl Tris-EDTA buffer. The PCR digest was subjected to electrophoresis on 3% Nusieve and the 108 bp fragment recovered by interception of the migrating band with DE81 paper. Ligation of the vector and PCR digested fragments was performed in a 20 µl reaction mixture consisting of 0.5 µl vector DNA, 0.1 µl PCR fragment, and 0.5 µl $T_4$ DNA ligase (New England Biolabs, Beverly, Mass.) in the buffer supplied by the manufacturer. The ligation was carried out at room temperature for 3 hours followed by transformation into $CaCl_2$ competent *E. coli* B. Plasmid DNA was prepared from two of the resulting transformants and dideoxy DNA sequencing was used to determine that the correct nucleotide sequence had been obtained. This plasmid was designated pUDBNP2 and encodes human ubiquitin fused in-frame to b-type natriuretic peptide (2-32).

Figure 4:
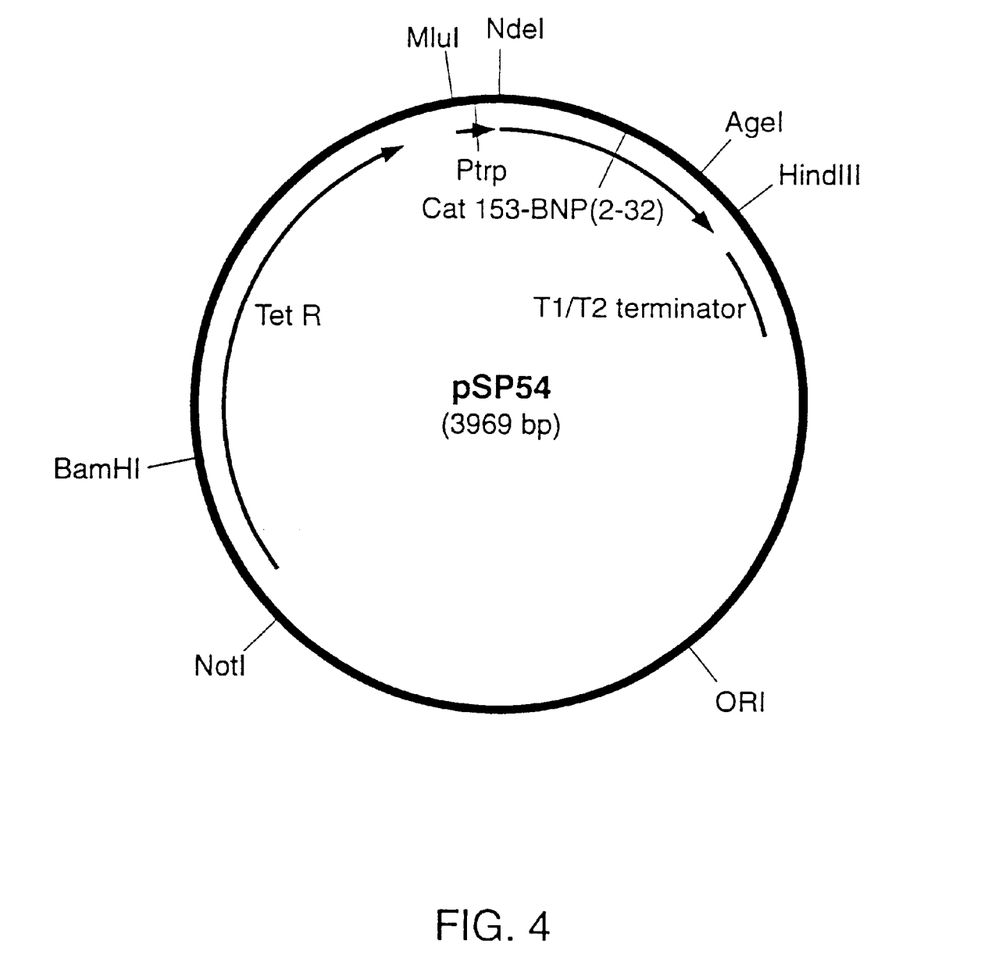
FIG. 4 is a plasmid diagram of pSP54.
Figure 5:
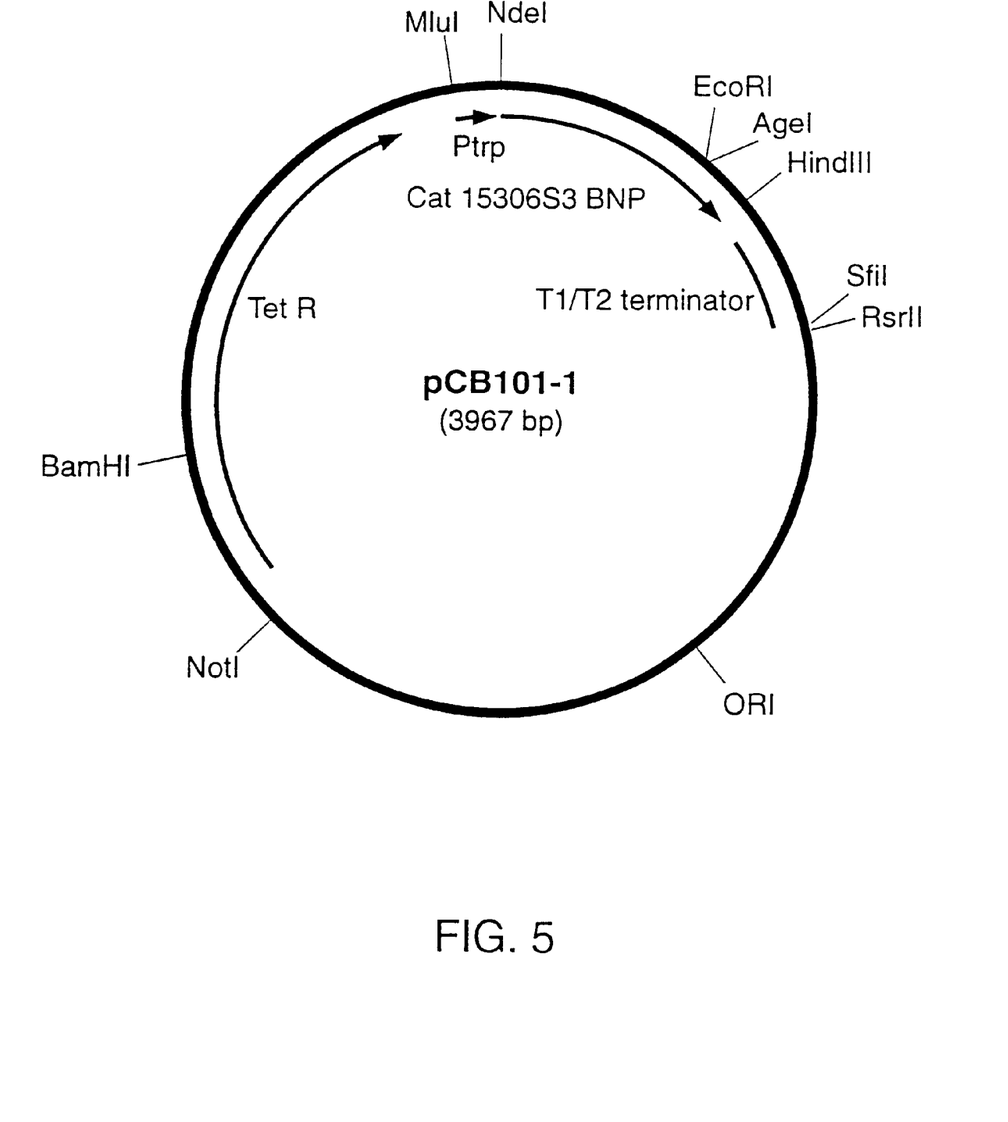
FIG. 5 is a plasmid diagram of pCB 101-1.
Figure 6:
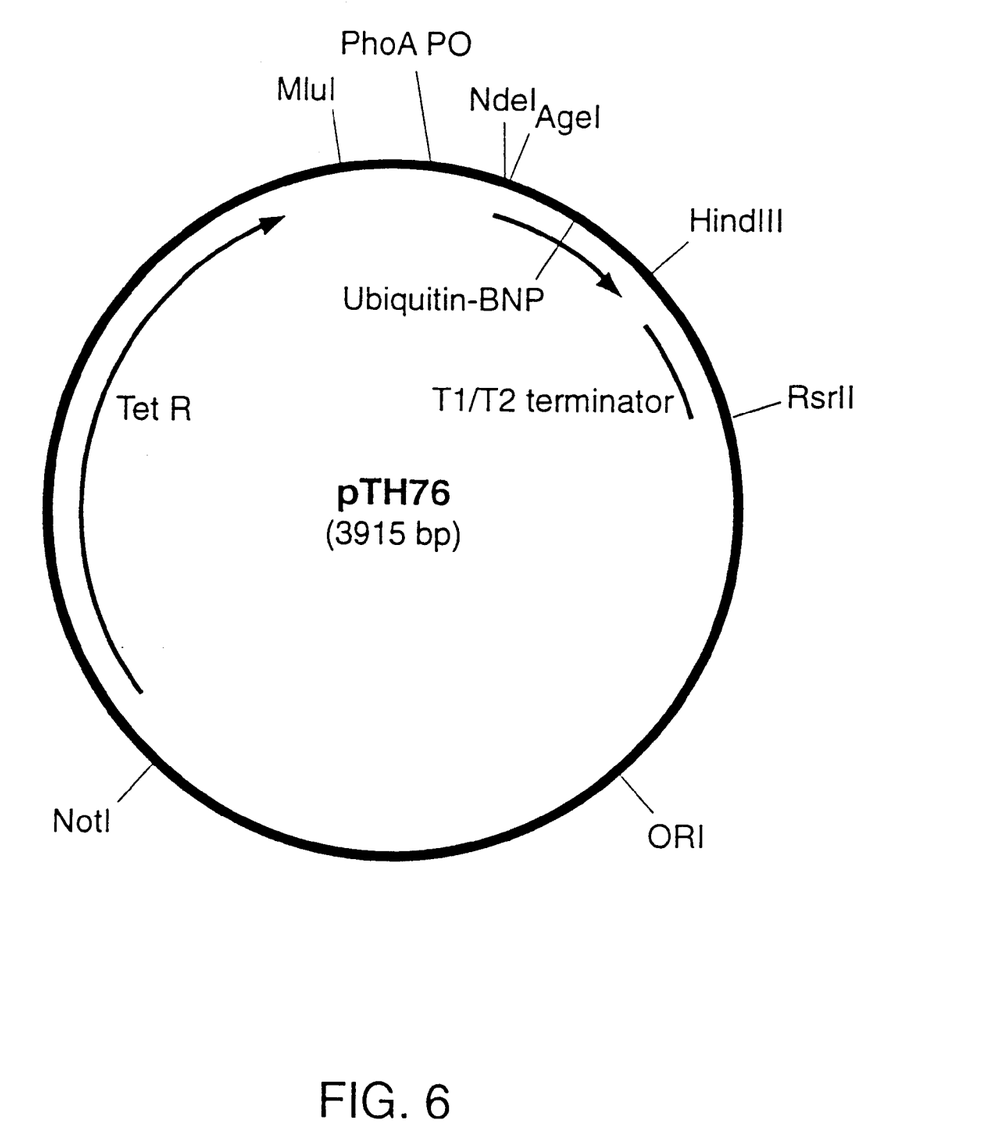
FIG. 6 is a plasmid diagram of pTH76.
Figure 7:
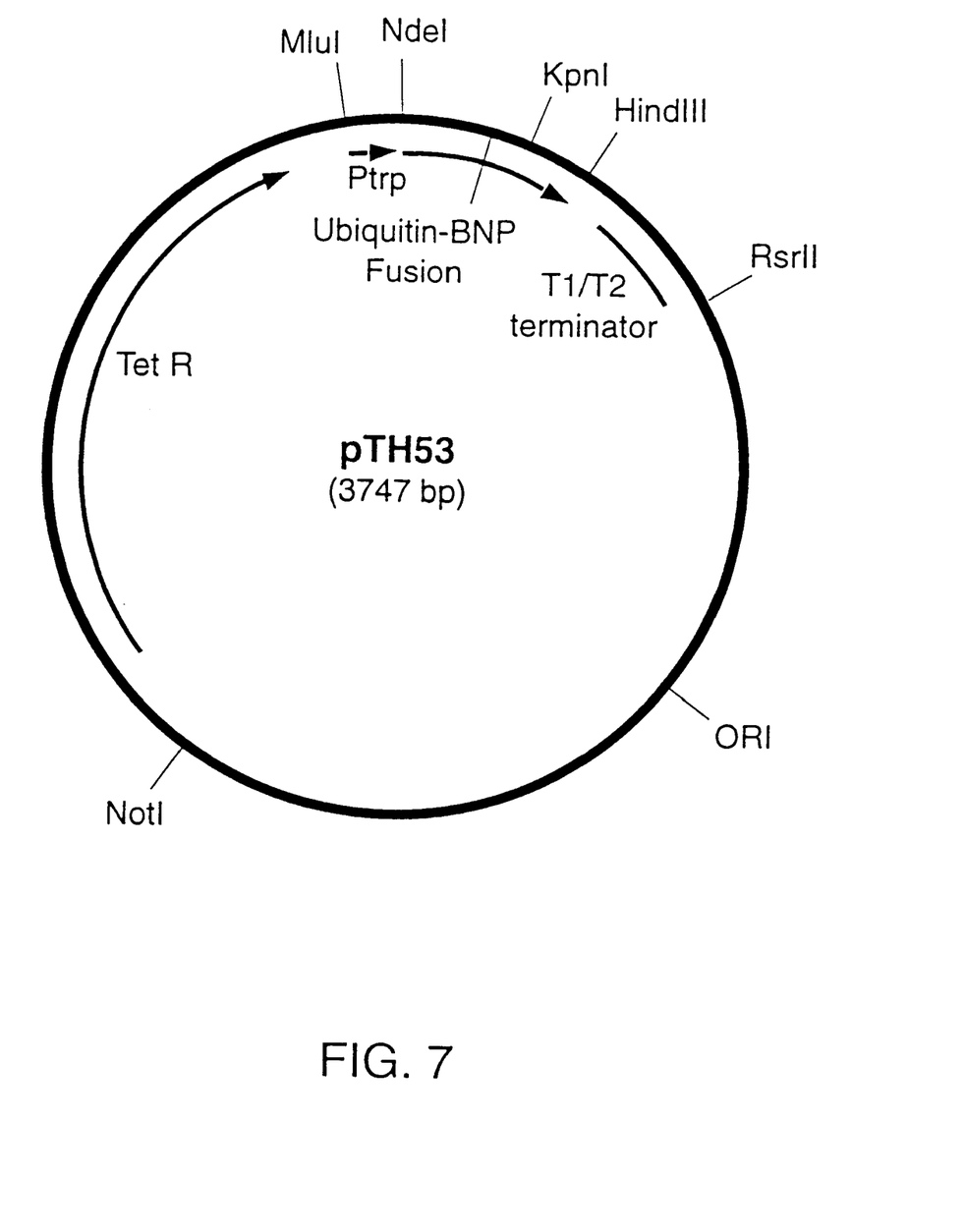
FIG. 7 is a plasmid diagram of pTH53.

For the construction of an expression plasmid expressing a gene fusion of CAT154 to b-type natriuretic peptide (2-32), plasmid pUDBNP2 was used as a source of the b-type natriuretic peptide (2-32) coding sequence while plasmid pCB101-1 encodes the CAT154 fusion partner and will be used as the recipient of the b-type natriuretic peptide (2-32) fragment. Five micrograms of pUDBNP2 and 1 µg of pCB 101-1 were each digested with AgeI in the buffer supplied by the manufacturer (New England Biolabs, Beverly, Mass.) for 2 hours at 37° C. Digests were checked for completion by agarose gel electrophoresis. DNA was recovered from the digestion mixture using GeneClean (Bio101, CA) and eluted in a final volume of 15 µl. Both plasmids were then digested with BamHI in the buffer supplied by the manufacturer (New England Biolabs, Beverly, Mass.) for 1.5 hours at 37° C. Agarose gel electrophoresis showed the pUDBNP2 digest to be incomplete, therefore the partially digested DNA was recovered using GeneClean and redigested BamHI as before. At this point, agarose gel electrophoresis showed both the pUDBNP2 and pCB-101-1 digests to be complete. Fragments for ligation were prepared by electrophoresis on 3% Nusieve excising the 2407 bp band from the pUDBNP2 digest and the 1562 bp band from the pCB101-1 digest. DNA fragments were recovered using Geneclean and eluted in a 10 μl final volume. Ligation of the two fragments was achieved using 2 μl of the pUDBNP2 DNA fragment and 5 μl of the DNA fragment from pCB101-1 in a mixture with 1 μl T$_4$ DNA ligase (New England Biolabs, Beverly, Mass.) in the buffer supplied by the manufacturer at 15° C. overnight. The resulting mix was transformed into CaCl$_2$ competent *E. coli* W3110. Plasmid DNA prepared from six of the resulting transformants was digested with BglI and plasmids having the correct structure were identified based on the presence of both 2845 bp and 890 bp fragments. An expected 234 bp band arising from the tetracycline resistance region is too small to be visualized. In addition, cultures used for plasmid DNA preparation were also inoculated into small LB cultures and incubated overnight at 37° C. The resulting cells were visualized by phase contrast microscopy while other aliquots were boiled in SDS sample buffer and analyzed by SDS polyacrylamide gel electrophoresis. Of the six colonies treated this way, the three that gave the correct restriction pattern also showed the presence of phase bright inclusion bodies in microscopy and the presence of a strong Coomassie staining band at approximately 20,500 daltons in SDS-PAGE. This plasmid was designated pSP54. FIG. 4 is a plasmid diagram of pSP54.

EXAMPLE 3

Production and Isolation of b-type Natriuretic Peptide (1-32)

(a) Fermentation and Cell Lysis

*E. coli* cells harboring the b-type natriuretic peptide (1-32) expression vector (pTH85/TEH 102) were fermented in fed-batch mode. Induction of fusion protein expression in this system is caused by allowing the cells to deplete the phosphate from the medium. Forty three liters of whole fermentation broth were harvested at the end of the fermentations. The resulting biomass was collected by centrifugation of whole fermentation broth in 1 L bottles and is stored at −70±10° C. The biomass yield from 43 liters of fermentation was 4.7 kg of wet weight *E. coli* cells. The frozen biomass was thawed overnight at room temperature and diluted to 25% w/v using lysis buffer (20 mM Na$_x$H$_x$PO$_4$, 5 mM EDTA, pH 6.0). The cells were homogenized using a Maton-Gaulin Model 30CD (9–10,000 psi) homogenizer with a refrigerated heat exchanger in line. The cell solution was chilled to 2° C. before initiating lysis and temperature maintained below 15° C. throughout the lysis. The flow through the homogenizer was routed back into the cell solution to allow an average of 6 passes through the homogenizer to achieve the homogenization endpoint of >90% lysis as gauged by microscopic examination.

(b) Inclusion Body Recovery by Batch Centrifugation

Batch centrifugation was performed in 1 L polypropylene bottles using a refrigerated Sorvall RC-3B centrifuge with H6000 rotor. The *E. coli* cell lysate was diluted with lysis buffer to 12.5% starting cell weight and centrifuged in a Sorvall RC-3B centrifuge equipped with an H6000A rotor at 4500 rpm (5894 g) for 40 minutes. Supernatant was decanted and the inclusion body pellet (905 g) stored at 2–8° C.

(c) Acid Cleavage Reaction

The acid cleavage reaction mixtures were prepared from the inclusion body preparation described above. The inclusion bodies were removed from 2–8° C. storage and re-suspended using a hand-held homogenizer to 1980 mL (100 g inclusion bodies/220 mL) with deionized water. An aliquot of this suspension equivalent to 100 g wet weight was further processed. The inclusion body preparation was diluted with 780 mL of deionized water to yield a 10% wet weight suspension. The pH of the inclusion body suspension was adjusted with concentrated hydrochloric acid (~4 mL) to 1.99. Vigorous stirring was required as the solution thickened between pH 4.5 and 3.0.

The above described inclusion body suspension was placed in a temperature controlled glass-lined reaction vessel equipped with stirring, sample port, and connections to provide an inert gas atmosphere. Inert gas was allowed to flow into the reaction vessel at 5 psi with the vent open. The temperature controller was turned on and adjusted to the appropriate setting. Timing of the reaction began at this point. Heating was allowed to proceed to 40° C. at which time the vent was closed and the reaction vessel allowed to pressurize to 5 psi. The reaction vessel was vented occasionally during the period of temperature adjustment to maintain this head pressure. The reaction mixture was within 5° C. of the desired temperature within 15 minutes. The temperature was controlled to 85±0.5° C. throughout the reaction period. Samples were taken at regular intervals (1 hour and 30 minutes) for RP-HPLC analysis of b-type natriuretic peptide release. Sampling was performed by first closing off the gas inlet valve then venting the vessel to atmospheric pressure and finally withdrawing a 1 mL sample from the sampling port with a disposable syringe. The sampling port was then closed off, the gas inlet valve re-opened, the vessel allowed to vent for 5–10 seconds and finally the vent closed to allow the vessel to re-pressurize.

The reaction was terminated after 4.5 hours by cooling to 2–8° C. on ice. The solution was continuously stirred during cooling. Reduction of temperature to <40° C. was achieved in <20 minutes. At the end of the cooling period the pH of the reaction mixture was adjusted to 2.9 with 2 N NaOH. The b-type natriuretic peptide content of this solution was determined by RP-HPLC peak area as 1.92 g b-type natriuretic peptide/L. This solution was frozen at −70±10° C. until further processing.

(d) IEC Purification of b-type Natriuretic Peptide (1-32) from Acid Cleavage Reaction Mixture For IEC purification of b-type natriuretic peptide (1-32) four acid cleavage reaction mixtures, prepared as described above, were combined and 260 g of solid urea were added to 1 L of acid cleavage reaction mixture to give a 3.5 M urea concentration. The final volume was 1.3 L. This solution contained 0.6 mg b-type natriuretic peptide/mL or 780 mg b-type natriuretic peptide. The solution was loaded onto a packed column of Whatman Express-Ion Exchanger S (sulfoxyethyl ion exchange resin) at 8 mg hBNP/mL resin, based on the RP-HPLC assay. The column was washed sequentially, with 200 mL 3.5 M urea, 50 mM acetic acid pH 3.5, 500 mL 50 mM acetic acid, 600 mL 10 mM dithiothreitol (DTT), 50 mM sodium phosphate pH 7.2, and finally with 1 L 55 mM NaCl in 50 mM sodium phosphate pH 6.8. Elution of the now fully reduced b-type natriuretic peptide from the column was performed with a step gradient of 1 L 500 mM NaCl in 50 mM sodium phosphate pH 6.8. The elution peak of 150 mL was collected and analyzed for b-type natriuretic peptide content (590 mg total). The elution pool was stored at −70±10° C. until further processing.

(e) Disulfide Bond Formation 145 mL of the ion exchange column eluant was thawed overnight at 4° C. and then allowed to warm to room temperature. The solution was diluted with 50 mM sodium phosphate pH 6.8 to 1.4 mg b-type natriuretic peptide/mL. Disulfide bond formation was accomplished by air oxidation at 35° C. for 6 hours with moderate stirring. The reaction was terminated by acidification to pH 5.0 by addition of 5 M acetic acid. The oxidation pool was stored at −70±10° C. until further processing.

(f) Reverse-Phase HPLC Purification of b-type Natriuretic Peptide

The oxidation pools from two oxidation reactions performed as described above were thawed to 2–8° C. overnight and allowed to warm to room temperature. The pH was adjusted to 5.5 with 5 N ammonium hydroxide. This solution (869 mg b-type natriuretic peptide in 756 mL) was loaded at 10.6 mL/min onto preparative RP-HPLC (Zorbax Pro 10/150 C8) with solvent mixing (Load:Buffer B 85:15) to obtain 6% acetonitrile in the load. Resin loading was 9.8 mg/mL resin. Elution was performed at the same flow rate according to the table outlined below. Buffer A is purified water, Buffer B is 40% acetonitrile, Buffer C is 1 M ammonium acetate pH 5.5.

| Step | Volume (mL) | Load % | Buffer A % | Buffer B % | Buffer C % |
|---|---|---|---|---|---|
| Load | 890 | 85 | | 15 | |
| Wash | 353 | | 60 | 15 | 25 |
| Gradient start | | | 60 | 15 | 25 |
| Gradient end | 441 | | 35 | 40 | 25 |
| Hold | 177 | | 35 | 40 | 25 |

Fractions of the elution peak were analyzed by analytical RP-HPLC and fractions of purity >96% were pooled. The RP-HPLC pool contained 406 mg b-type natriuretic peptide (1-32).

(g) Characterization of b-type Natriuretic Peptide (1–32) from Acid Cleavage Reaction The main RP-HPLC peak from a similar preparation of b-type natriuretic peptide after acid cleavage, IEC chromatography, and RP-HPLC was characterized by complete N-terminal amino acid sequencing, amino acid analysis and electrospray mass spectrometry. In all respects, the peptide produced by this procedure was indistinguishable from synthetic b-type natriuretic peptide standard.

EXAMPLE 4

Purification of b-type Natriuretic Peptide (1-32) from Acid Cleavage Reaction Mixture by Ultrafiltration/Diafiltration As an alternative to solubilization of the acid cleavage reaction mixture for chromatography, the soluble b-type natriuretic peptide can be isolated from the crude acid cleavage reaction mixture by diafiltration. The reduced b-type natriuretic peptide passes through the filter and the higher molecular weight aggregates and insoluble material are retained. B-type natriuretic peptide passes freely through the membrane and is found in the filtrate.

A Filtron ultrasette filter with nominal molecular weight cut-off of 300 kD (Filtron, Cat #OS100C72) was set up in diafiltration mode according to the manufacturer's instruction. The device was washed with distilled $H_2O$ and then equilibrated with 20 mM sodium acetate, 150 mM sodium chloride, pH 4.0.

One liter of acid cleavage reaction mixture was prepared as described above. This solution contained 705 mg reduced b-type natriuretic peptide as determined by RP-HPLC peak area (RT 112/123, Jan. 26, 1996). This solution was placed in a 2 L Pyrex bottle and 60 mL of 5 M sodium chloride were added. The mixture was stirred on ice for 25 minutes and then 60 mL of distilled water and 100 mL of 0.2 M sodium acetate pH 4.0 were added. Stirring was continued for another 20 minutes on ice. The mixture was then circulated through the diafiltration device using a peristaltic pump with the circulation rate maintained at 2 L/min. The filtrate outlet was completely closed at the initiation of circulation. After approximately two minutes of circulation, the filtrate outlet was slowly opened and the filtrate flow rate was controlled at an average rate of 53.5 mL/min (range 25–82 mL/min). Diafiltration buffer, 20 mM sodium acetate, 150 mM sodium chloride, pH 4.0 was added to the 2 L bottle at the same rate as filtrate was removed from the filter in order to maintain the diafiltration solution at constant volume. At these settings, transmembrane pressure was maintained at <10 psi throughout the entire diafiltration process. After total of 5,700 mL of filtrate were collected, the addition of diluent to the diafiltration solution was stopped. An additional 1 L of filtrate was collected before the diafiltration process was completed. At the end of the diafiltration process a total volume of 6.7 L of filtrate had been collected. Quantitation of b-type natriuretic peptide in the filtrate by RP-HPLC showed a recovery of 550 mg b-type natriuretic peptide or 78%.

EXAMPLE 5

Production and Isolation of b-type Natriuretic Peptide (2-32)

(a) Fermentation and Cell Lysis

E. coli cells harboring the b-type natriuretic peptide (2-32) expression vector pSP54 were fermented in fed-batch mode. This system uses the trp promoter and fusion protein expression is induced by the addition of indole acrylic acid. Whole fermentation broth (4.7 liters) were harvested at the end of the fermentation. The resulting biomass was collected by centrifugation of whole fermentation broth in 1 L bottles and stored at −70±10° C. The biomass yield from 4.7 liters of fermentation was 432 g of wet weight E. coli cells. The frozen biomass was thawed overnight at room temperature and diluted to 25% w/v using crack buffer (20 mM $Na_xH_xPO_4$, 5 mM EDTA, pH 6.0). The cells were homogenized using a AVP Gaulin Model 30CD (9–10,000 psi) with a refrigerated heat exchanger in line. The cell solution was chilled to 2° C. before initiating breakage and temperature maintained below 15° C. throughout the lysis. The flow through the homogenizer was routed back into the cell solution to allow an average of 4 passes through the homogenizer to achieve the homogenization endpoint of >90% breakage as gauged by microscopic examination.

(b) Inclusion Body Recovery by Batch Centrifugation

Batch centrifugation was performed in 1 L polypropylene bottles using a refrigerated Sorvall RC-3B centrifuge with H6000 rotor. The E. coli cell lysate was diluted with lysis buffer to 12.5% starting cell weight and centrifuged in a Sorvall RC-3B centrifuge equipped with an H6000A rotor at 4500 rpm (5894 g) for 40 minutes. Supernatant was decanted and the inclusion body pellet (111.5 g) stored at −70±10° C.

(c) Acid Cleavage Reaction

The acid cleavage reaction mixture was prepared from the inclusion body preparations described above. Inclusion bodies (55.8 g) were removed from ±70±10° C. storage and re-suspended using a hand-held homogenizer to 558 mL with deionized water to yield a 10% wet weight suspension. The pH of the inclusion body suspension was adjusted with 1 M hydrochloric acid (~28 mL) to 2.0. Vigorous stirring was required as the solution thickens between pH 4.5 and 3.0.

The inclusion body preparation was placed a temperature controlled, glass-lined reaction vessel equipped with stirring, sample port, and connections to provide an inert gas atmosphere. Inert gas (Ar) was allowed to flow into the reaction vessel at 5 psi with the vent open. The temperature controller was turned on and adjusted to the appropriate setting. Timing of the reaction began at this point. Heating was allowed to proceed to 40° C. at which time the vent was closed and the reaction vessel allowed to pressurize to 5 psi. The reaction vessel was vented occasionally during the period of temperature adjustment to maintain this head pressure. The reaction mixture was within 5° C. of the desired temperature within 15 minutes. The temperature was controlled to 85±1.5° C. throughout the reaction period. Samples were taken at regular intervals (30 minutes) for RP-HPLC analysis of b-type natriuretic peptide (2-32) release. Sampling was performed by first closing off the gas inlet valve then venting the vessel to atmospheric pressure and finally withdrawing a 1 mL sample from the sampling port with a disposable syringe. The sampling port was then closed off, the gas inlet valve re-opened, the vessel allowed to vent for 5–10 seconds and finally the vent closed to allow the vessel to re-pressurize.

The reaction was terminated after 2.0 hours by cooling to 20° C. on ice. The solution was continuously stirred during cooling. At the end of the cooling period 28 mL of 1 M phosphoric acid was added to the reaction mixture (50 mM final) and the pH of the reaction mixture was adjusted to 2.8 with 10 N NaOH. The b-type natriuretic peptide (2-32) content of this solution was determined by RP-HPLC assay as 0.45 g reduced b-type natriuretic peptide (2-32)/L (223 mg total reduced b-type natriuretic peptide (2-32)). This solution were frozen at −70±10° C. until further processing.

(d) Batch Ion Exchange Purification of b-type Natriuretic Peptide (2-32) from Acid Cleavage Reaction Mixture B-type natriuretic peptide (2-32) was adsorbed from the pH-adjusted acid cleavage reaction mixture by batch incubation with SP-Spherodex LS cation exchange resin. 500 mL of the acid cleavage reaction mixture described above were thawed in a warm water bath for 1.5 hours, until the temperature reached 22° C. SP-Spherodex LS resin (50 mL), washed according to the manufacturer's instructions, were added to the thawed reaction mixture in a glass vessel with moderate stirring. The mixture was stirred for 90 minutes at ambient temperature and samples of supernatant were taken at 30 minute intervals. The resin was allowed to settle at the end of mixing for 5 minutes. The supernatant was decanted and the resin washed three times with 250 mL of 50 mM acetic acid. The resin was then packed in a column (2.5×11.5 cm) and further washed with 2 column volumes (CV) 50 mM acetic acid pH 3.5 at 8 mL/min. The column was then washed with 4 CV 50 mM sodium phosphate pH 7.2. On-column reduction was performed by washing the column with 4 CV 10 mM dithiothreitol (DTT) 50 mM sodium phosphate pH 7.2. Finally the column was washed with 4 CV of 50 mM sodium phosphate pH 7.2 followed by 5 CV of 50 mM sodium phosphate pH 7.2 containing 200 mM NaCl. Elution of the now fully reduced b-type natriuretic peptide (2-32) from the column was performed in two steps at 450 mM and 1 M NaCl in 50 mM sodium phosphate pH 7.2. The elution pool of 330 mL was collected and analyzed for b-type *.natriuretic peptide (2-32) content (148 mg total, 66% yield). The elution pool directly proceeded to disulfide bond formation.

(e) Disulfide Bond Formation b-type Natriuretic Peptide (2-32)

The 330 mL of ion exchange column eluant contained 0.45 mg b-type natriuretic peptide(2-32)/mL was pH adjusted to pH 6.8 with 2N HCl. Disulfide bond formation was accomplished by addition of 11 mL 15 mM $K_3Fe(CN)_6$ to the solution under argon at 2–8° C. for 11 hours. The reaction was terminated by acidification to pH 5.0 by addition of 3.4 mL 5 M acetic acid. The yield from the oxidation reaction was 121 mg b-type natriuretic peptide (2-32), an 82% step yield. The oxidation pool was stored at 2–8° C. overnight.

(f) Reverse-Phase HPLC Purification of b-type Natriuretic Peptide (2-32)

The oxidation pool was allowed to warm to room temperature and was further purified by RP-HPLC. Acetonitrile (18 mL) was added to 342 mL of oxidation pool to give 360 mL of load. The pH was adjusted to 5.5 with 10 N ammonium hydroxide. This solution (160 mL containing 51 mg b-type natriuretic peptide (2-32)) was loaded at 4.5 mL/min onto the RP-HPLC column (Vydac C4 214TP1010). Resin loading was 3 mg/mL. Elution was performed at the same flow rate, according to the table outlined below. Buffer A is 5% acetonitrile, 50 mM ammonium acetate pH 5.0, Buffer B is 50% acetonitrile, 50 mM ammonium acetate pH 5.0.

| Step | Volume (mL) | Load % | Buffer A % | Buffer B % |
| --- | --- | --- | --- | --- |
| Load | 160 | 100 | | |
| Wash | 67.5 | | 100 | |
| Gradient start | | | 100 | |
| Gradient end | 180 | | 60 | 40 |

Fractions of the elution peak were collected manually, analyzed by analytical RP-HPLC and stored at 2–8° C. for 3 days prior to pooling. Fractions of purity >95% were pooled to give a final pool of >97% purity by analytical RP-HPLC and yield of 48 mg b-type natriuretic peptide (2-32) or 94% step yield.

(g) Characterization of b-type Natriuretic Peptide (2-32) from Acid Cleavage Reaction The main RP-HPLC peak from a similar preparation of b-type natriuretic peptide after acid cleavage, IEC chromatography, and RP-HPLC was characterized by complete N-terminal amino acid sequencing, amino acid analysis, and electrospray mass spectrometry. The results of all three assays indicated that the peptide produced by this protocol was b-type natriuretic peptide (2-32).

What is claimed is:

1. A method for producing a purified peptide having a pI below 5 or above 8 which comprises:
  (a) expressing said peptide having a pI below 5 or above 8, in a recombinant host cell, as a fusion protein in which the peptide is fused at its N-terminus, to a fusion partner comprising an amino acid sequence having an Asp residue at its C-terminus, wherein (i) the C-terminal Asp residue of the fusion partner and the N-terminal residue of the peptide form a bond which is cleavable under acidic conditions, (ii) the peptide has a different net charge from that of the fusion partner and any undesired fragments produced by the acid cleavage of the fusion partner to allow it to be separated from the fusion partner and any undesired acid cleavage fragments of the fusion protein by ion-exchange chromatography and (iii) the fusion protein forms inclusion bodies within the recombinant host cell;
  (b) recovering the inclusion bodies from the recombinant host cell;
  (c) cleaving the peptide from the fusion partner by subjecting the fusion protein to acidic conditions in the absence of a chaotrope;
  (d) solubilizing insoluble cleavage products by treating them with 3.5 M urea, so that the primary structure of the peptide is not degraded; and
  (e) isolating the peptide by ion-exchange chromatography.

2. The method as claimed in claim 1, wherein the fusion partner has a net charge such that said fusion protein has a pI between 6.0 and 8.0.

3. The method as claimed in claim 1, wherein the fusion partner has a net charge such that said fusion protein has a pI between 6.5 and 7.5.

4. The method of claim 1, comprises diluting the isolated peptide with 50 mM sodium phosphate pH 6.8 and subjecting the isolated peptide to air oxidation at 35° C. for 6 hours, such that a biologically active peptide is produced.

5. The method in claim 1, wherein the desired peptide contains no internal dipeptide sequences that is cleavable under acid conditions.

6. The method in claim 1, wherein the peptide contains one or more internal dipeptide sequences that are cleavable under acid conditions at a cleavage rate less than that of the dipeptide formed by the C-terminal amino acid residue of the fusion partner and the N-terminal acid residue of the peptide.

7. The method of claim 1, wherein the peptide is b-type natriuretic peptide.

8. The method of claim 1, wherein the non-ionic chaotrope employed in step (d) is urea.

9. The method of claim 7, wherein the peptide is treated with urea at a concentration of from about 3 M to about 7 M.

10. The method of claim 9, wherein the peptide is b-type natriuretic peptide.

11. A method for producing a purified peptide having a pI below 5 or above 8 which comprises:
  (a) expressing said peptide, in a recombinant host cell, as a fusion protein in which the desired peptide is fused at its N-terminus, to a fusion partner comprising an amino acid sequence having an Asp residue at its C-terminus, wherein (i) the C-terminal Asp residue of the fusion partner and the N-terminal residue of the peptide form a bond which is cleavable under acidic conditions, (ii) the peptide has different net charge from that of the fusion partner and any undesired fragments produced by the acid cleavage of the fusion partner to allow it to be separated from the fusion partner and any undesired acid cleavage fragments of the fusion protein by ion-exchange chromatography and (iii) the fusion protein forms inclusion bodies with the recombinant host cell;
  (b) recovering the inclusion bodies from the recombinant host cell;
  (c) cleaving the peptide from the fusion partner by subjecting the fusion protein to acidic conditions in the absence of a chaotrope;
  (d) removing insoluble cleavage products from the cleavage mixture by ultrafiltration, diafiltration or centrifugation; and
  (e) isolating the peptide by ion-exchange chromatography.

12. The method of claim 11, wherein the peptide is subjected to one or more additional purification steps subsequent to step (e).

13. The method of claim 12, wherein the peptide is b-type natriuretic peptide and it is subjected, sequentially to reverse phase HPLC chromatography and an additional ion-exchange chromatography subsequent to step (e).

14. A vector for the expression in a host cell of a fusion protein that is cleavable under acid conditions to yield a desired peptide having a pI above 8 or below 5, comprising:
 (a) a DNA sequence encoding a fusion protein partner with a net charge such that the fusion protein has a pI between 6.0 and 8.0;
 (b) a codon encoding aspartic acid, which is linked to the 3' end of the DNA sequence encoding the fusion protein partner of step (a);
 (c) a DNA sequence encoding a desired peptide having a pI above 8 or below 5 and having a proline, glycine, serine, leucine, alanine, isoleucine or valine residue at its N-terminus, said sequence being linked at its 5' end to the 3' end of the codon encoding aspartic acid of step b; and
 (d) a regulatory sequence capable of directing expression of the fusion protein in the host cell which is operably linked to the DNA sequence.

15. A vector as claimed in claim 14, wherein the fusion protein partner is the chloramphenicol acetyl transferase of SEQ ID NO: 12.

16. A vector as claimed in claim 14, wherein the encoded fusion partner has a net charge such that said fusion protein has a pI from 6.5 to 7.5.

17. A vector as claimed in claim 14, wherein the desired peptide is b-type natriuretic peptide.

18. A vector as claimed in claim 14, wherein the regulatory sequence includes a phoA promoter.

19. A vector as claimed in claim 14, wherein the fusion partner contains at least 50 residues corresponding to the 50 N-terminal amino acid residues of SEQ ID NO: 11.

20. A host cell containing the vector of claim 14.

21. A host cell containing the vector of claim 15.

22. A host cell containing the vector of claim 16.

23. A host cell containing the vector of claim 17.

24. A host cell containing the vector of claim 18.

25. A host cell containing the vector of claim 19.

26. The method of claim 1, wherein said recombinant host cell is a prokaryotic organism.

27. The method of claim 26, wherein said prokaryotic organism is *Escherichia coli*.

\* \* \* \* \*

SEQUENCE LISTING

<160> NUMBER OF SEQ ID NOS: 14

<210> SEQ ID NO 1
<211> LENGTH: 37
<212> TYPE: DNA
<213> ORGANISM: Artificial Sequence
<220> FEATURE:
<223> OTHER INFORMATION: Cloning oligonucleotide

<400> SEQUENCE: 1
tatggagaaa aaaatcactg gatataccac cgttgat                                    37

<210> SEQ ID NO 2
<211> LENGTH: 56
<212> TYPE: DNA
<213> ORGANISM: Artificial Sequence
<220> FEATURE:
<223> OTHER INFORMATION: Cloning oligonucleotide

<400> SEQUENCE: 2
cagaacatga tattgggata tatcaacggt ggtatatcca gtgattttt tctcca              56

<210> SEQ ID NO 3
<211> LENGTH: 60
<212> TYPE: DNA
<213> ORGANISM: Artificial Sequence
<220> FEATURE:
<223> OTHER INFORMATION: Cloning oligonucleotide

<400> SEQUENCE: 3
atatcccaat atcatgttct ggaacatttt gaggcatttc agtcagttgc tcaatcaacc         60

<210> SEQ ID NO 4
<211> LENGTH: 60
<212> TYPE: DNA
<213> ORGANISM: Artificial Sequence
<220> FEATURE:
<223> OTHER INFORMATION: Cloning oligonucleotide

<400> SEQUENCE: 4
tataaccaga ccgttcagct ggatattacg gccttttag aaaccgtaga agttaatgtt          60

<210> SEQ ID NO 5
<211> LENGTH: 60
<212> TYPE: DNA
<213> ORGANISM: Artificial Sequence
<220> FEATURE:
<223> OTHER INFORMATION: Cloning oligonucleotide

<400> SEQUENCE: 5
aaaggccgga taaacaggt gaacattaac ttctacggtt ctaaaaagg ccgtaatatc           60

<210> SEQ ID NO 6
<211> LENGTH: 60
<212> TYPE: DNA
<213> ORGANISM: Artificial Sequence
<220> FEATURE:
<223> OTHER INFORMATION: Cloning oligonucleotide

<400> SEQUENCE: 6
cagctgaacg gtctggttat aggttgattg agcaactgac tgaaatgcct caaaatgttc        60

<210> SEQ ID NO 7
<211> LENGTH: 64
<212> TYPE: DNA
<213> ORGANISM: Artificial Sequence
<220> FEATURE:
<223> OTHER INFORMATION: Cloning oligonucleotide

<400> SEQUENCE: 7
cacctgtttt atccggcctt tattcacatt cttgccgttc tgctgaatgc tcatccgctg        60
ttca                                                                      64

<210> SEQ ID NO 8

```
<211> LENGTH: 47
<212> TYPE: DNA
<213> ORGANISM: Artificial Sequence
<220> FEATURE:
<223> OTHER INFORMATION: Cloning oligonucleotide

<400> SEQUENCE: 8
ccggtgaaca gcggatgagc attcagcaga acgggaagaa tgtgaat          47

<210> SEQ ID NO 9
<211> LENGTH: 35
<212> TYPE: DNA
<213> ORGANISM: Artificial Sequence
<220> FEATURE:
<223> OTHER INFORMATION: PCR primer

<400> SEQUENCE: 9
gtggtggtac cggtggtgac ccgaaaatgg ttcag                        35

<210> SEQ ID NO 10
<211> LENGTH: 20
<212> TYPE: DNA
<213> ORGANISM: Artificial Sequence
<220> FEATURE:
<223> OTHER INFORMATION: PCR primer

<400> SEQUENCE: 10
cctactctcg catggggaga                                         20

<210> SEQ ID NO 11
<211> LENGTH: 79
<212> TYPE: PRT
<213> ORGANISM: Artificial Sequence
<220> FEATURE:
<223> OTHER INFORMATION: Synthetic wild type chloramphenicol acetyl
      transferase amino terminal region

<400> SEQUENCE: 11

Met Glu Lys Lys Ile Thr Gly Tyr Thr Thr Thr Val Asp Ile Ser Gln
 1               5                  10                  15

Trp His Arg Lys Glu His Phe Glu Ala Phe Gln Ser Val Ala Gln Cys
            20                  25                  30

Thr Tyr Asn Gln Thr Val Gln Leu Asp Ile Thr Ala Phe Leu Lys Thr
        35                  40                  45

Val Lys Lys Asn Lys His Lys Phe Tyr Pro Ala Phe Ile His Ile Leu
    50                  55                  60

Ala Arg Leu Met Asn Ala His Pro Glu Phe Arg Met Ala Met Lys
65                  70                  75

<210> SEQ ID NO 12
<211> LENGTH: 79
<212> TYPE: PRT
<213> ORGANISM: Artificial Sequence
<220> FEATURE:
<223> OTHER INFORMATION: Synthetic modified chloramphenicol acetyl
      transferase amino terminal region

<400> SEQUENCE: 12

Met Glu Lys Lys Ile Thr Gly Tyr Thr Thr Thr Val Asp Ile Ser Gln
 1               5                  10                  15

Tyr His Val Leu Glu His Phe Glu Ala Phe Gln Ser Val Ala Gln Ser
            20                  25                  30

Thr Tyr Asn Gln Thr Val Gln Leu Asp Ile Thr Ala Phe Leu Glu Thr
        35                  40                  45
```

```
Val Glu Val Asn Val His Leu Phe Tyr Pro Ala Phe Ile His Ile Leu
    50                  55                  60

Ala Val Leu Leu Asn Ala His Pro Leu Phe Thr Gly Gly Pro Asp
65                  70                  75
```

<210> SEQ ID NO 13
<211> LENGTH: 44
<212> TYPE: DNA
<213> ORGANISM: E. coli

<400> SEQUENCE: 13
tgtttttatt ttttaatgta tttgtacatg gagaaaataa agtg         44

<210> SEQ ID NO 14
<211> LENGTH: 43
<212> TYPE: DNA
<213> ORGANISM: Artificial Sequence
<220> FEATURE:
<223> OTHER INFORMATION: Artificial phoA promoter sequence

<400> SEQUENCE: 14
tgtttttatt ttttaatgta tttgtacaag aggcttccat atg          43